United States Patent [19]

McRae

[11] Patent Number: Plant 5,898

[45] Date of Patent: Mar. 10, 1987

[54] ASIATIC LILY NAMED VANESSA

[75] Inventor: Edward A. McRae, Boring, Oreg.

[73] Assignee: Melridge, Inc., Gresham, Oreg.

[21] Appl. No.: 710,496

[22] Filed: Mar. 11, 1985

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Charles W. Rummler; John B. Lungmus

[57] ABSTRACT

A new variety of hybrid Asiatic lily having large compact racemes of flowers of large size and excellent form, with an intense and unusual color pattern, and having long persistence, both on the plant and as cut flowers. The flowers of this new plant are particularly characterized by their unusual combination of yellow and gold color tones with very light maculation providing a color pattern that is new in the upright Asiatic division of lilies. The plant itself is highly resistant to disease and shows high tolerance to virus, making it an excellent garden plant. The bulbs may be precooled and forced for cut flowers, which are produced in mid-season, between the flowering times of its siblings, thereby broadening the entire season of cut flower production.

1 Drawing Figure

BACKGROUND OF THE INVENTION

My new variety of Asiatic lily originated as a seedling selected from a group resulting from my crossing the variety "*flavum*" of the species *Lilium wilsonii* with the cultivar "Connecticut King" as the pollen parent. This crossing was done in the course of breeding efforts carried on by me at Sandy, Oreg., since 1971 with the object of producing new and superior varieties of upright flowering Asiatic lilies suited to cut flower production and representing a range of flowering times to extend and broaden the season of cut flower production of Asiatic lily blooms.

The yellow and gold flowers of this new lily plant are particularly characterized by their large size and very broad tepals of thick texture, each yellow tepal being flushed with gold at its base portion with very light spotting on opposite sides of the nectaries thereby forming an unusual color pattern.

The discovery plant of my new variety of Asiatic lily has been asexually reproduced by me and under my direction at Sandy, Oreg., and as observed at Sandy, Oreg., the clone appears to possess very desirable characteristics of hybrid vigor and great hardiness with vigorous growing habits and good propagating characteristics and a high degree of disease resistance, as observed at Sandy, Oreg.

Successive generations of my new plant produced by bulb scale propagation and natural propagation from bulblets have demonstrated that the novel and distinctive characteristics of my new variety hold true from generation to generation and appear to be firmly fixed.

DESCRIPTION OF THE DRAWING

This new variety of Asiatic lily is illustrated in the accompanying full color photographic drawing which shows a three-quarter face view of the open bloom illustrating the flower form, the tepal arrangement, and in particular, the novel and distinctive yellow and gold color pattern with its very light maculation of the unusually broad tepals.

DESCRIPTION OF THE NEW PLANT

The following is a detailed description of my new variety of Asiatic lily plant as observed at Sandy, Oreg., with color designations according to The R.H.S. Colour Chart published by The Royal Horticultural Society of London, England, and with nomenclature according to The International Lily Register, Second Edition, of The Royal Horticultural Society.

THE PLANT

Origin: Seedling.

Parentage:

*Seed parent.*—*Lilium wilsonii* var. *flavum* (unpatented).

*Pollen parent.*—Connecticut King (unpatented).

Classification:

*Botanic.*—Hybrid lily cultivar, Division 1-A of the Horticultural Classification of Lilies By The Royal Horticultural Society.

*Commercial.*—Asiatic hybrid lily.

Form: Single stem, erect and stately.

Height: 120 to 170 cm., from bulbs 15 to 20 cm. in circumference.

Growth: Vigorous and upright.

Foliage:

*Quantity.*—Abundant.

*Leaf size.*—About 8 to 12 cm. long and about 1.5 to 2 cm. wide adjacent the base.

*Leaf shape.*—Lanceolate with acuminate tip and entire margins.

*Texture.*—Leathery.

*Aspect.*—Glossy.

*Color.*—Medium green.

Bulbs:

*Size.*—Ranging up to about 25 cm. in circumference for commercial use.

*Color.*—White.

THE BUD

Form: Obtuse, fluted and long oblong.

Size: About 7 to 9 cm. long just prior to opening.

Opening rate: The bud opens slowly (about one hour) at maturity, in response to light.

Color: Medium to deep yellow when the outer tepals first divide and also when the tepals begin to unfurl.

Tepals when unfurling:

*Color.*—Medium to deep yellow on top and under sides with the upper surface adjacent the nectaries flushed with gold.

Peduncle: About 7 to 10 cm. long, depending upon light levels.

*Color.*—Medium green.

THE FLOWER

Blooming habit: Annually in mid-season for Asiatic lilies. October dug bulbs, properly precooled and planted under glass with no supplementary lighting when planted in February in western Oregon, flower in about 90 to 95 days.

Size: Large; about 15 to 18 cm. in diameter.

Borne: In compact raceme having 5 to 8 blooms on a single stem.

Shape: Flat to slightly cup-shaped with tepal tips lightly recurved.

Tepalage:

*Number.*—Six.

*Arrangement.*—Imbricated.

*Shape.*—Elliptic with acute tip and entire margins.

*Texture.*—Leathery.

*Appearance.*—Shiny.

*Color.*—Yellow, RHS 12 A-B, each tepal having a flush of Gold, RHS 21A, about 2 cm. wide and about 2 cm. or more long above the nectary and along the tepal midrib, each tepal having a small group of magenta colored spots adjacent the tepal base and on each side of the mectary.

Pedicels: 4 to 6 cm. long.

*Color.*—Light green.

*Form.*—Sturdy and upright.

Color change: As the flower ages, color intensifies slightly and may become more golden-toned under low light levels.

Persistence: Tepals stay on the stem about 3 weeks.

Fragrance: None.

Disease resistance: Flower and plant are resistant to Fusarium and Botrytis.

Lasting quality: The flower is long lasting, both on the plant and as a cut flower.

REPRODUCTIVE ORGANS

Stamens:

*Number.*—Six.

*Anthers.*—Color: Greyed Gold, RHS 167A.

*Filaments.*—Length: About 5 cm. Color: Ivory or yellow.

*Pollen.*—Same as anthers.

Pistils:

*Number.*—One.

*Length.*—About 5 cm.

*Stigma.*—Color: Light plum to gold.

Character of ovary: Typical of genus Lilium.

THE FRUIT

Fertility: The fruit is fertile.

Shape: Ovoid.

Color at maturity: Soft brown, sometimes overlaid with light plum.

This new variety of hybrid Asiatic lily most nearly resembles Connecticut King (unpatented) but has much broader tepals with very few spots adjacent the nectary. The new plant is taller and is superior for year-round forcing. It flowers somewhat later than Connecticut King but in the meantime, the flowering of its siblings, which have been selected for commercial cut flower production, materially broadens the cut flower season for this type of lily.

Distinguishing Characteristics of Siblings
From the Cross *Lilium Wilsonii* var. *flavum* x "Connecticut King"

| Cv | Days to Bloom | Buds | Maculation |
|---|---|---|---|
| Pollyanna Ser. No. 710,427 | 80–85 | 5–8 | Heavy, large. |
| Joanna Ser. No. 710,457 | 80 | 5–7 | Light |
| Adelina Ser. No. 710,614 | 80–85 | 6–8 | Very few and small. Of deep magenta color. |
| Vanessa Ser. No. 710,496 | 90–95 | 5–8 | Very light |
| Yolanda Ser. No. 710,577 | 95–100 | 5–8 | Sparse and of deep magenta color. |
| Gold Medal (Half Sib) Ser. No. 710,592 | 60–70 | 6–8 | Few, tiny |

| Cv | Other Notable Characteristics |
|---|---|
| Pollyanna Ser. No. 710,427 | Relatively narrow, widely spaced tepals and sepals with very little marginal overlapping. Arrangement, hexagonal. |
| Joanna Ser. No. 710,457 | Tepal-sepal angle 60°. Arrangement, generally imbricated. |
| Adelina Ser. No. 710,614 | Tepals are large, thick textured, relatively broad, and with lightly recurved tips. Arrangement, imbricated. |
| Vanessa Ser. No. 710,496 | Tepals have slightly recurved tips and inconspicuous maculation. Arrangement, uniformly imbricated. |
| Yolanda Ser. No. 710,577 | Larger bulb, flower dished with tepal-sepal angle 60°, with lightly overlapping arrangement. |
| Gold Medal (Half Sib) Ser. No. 710,592 | Very thick and broad tepals in 60° overlapping arrangement with sepals, Unusually long lasting flowers, bud blast resistant when forced, and attains large bulb size only in season. |

I claim:

1. A new and distinct variety of hybrid Asiatic lily plant, substantially as herein shown and described, characterized in particular by its yellow and gold flower color pattern and its relatively light maculation, which features are unique in the Asiatic hybrid division of lilies suited to forcing and commercial cultivation; by its vigorous growth and propagation characteristics; the excellence of its flower form and substance; its versatility both as a garden plant and as a plant produced from precooled bulbs forced for cut flower production; and its unique mid-season time of flowering to broaden the cut flower season.

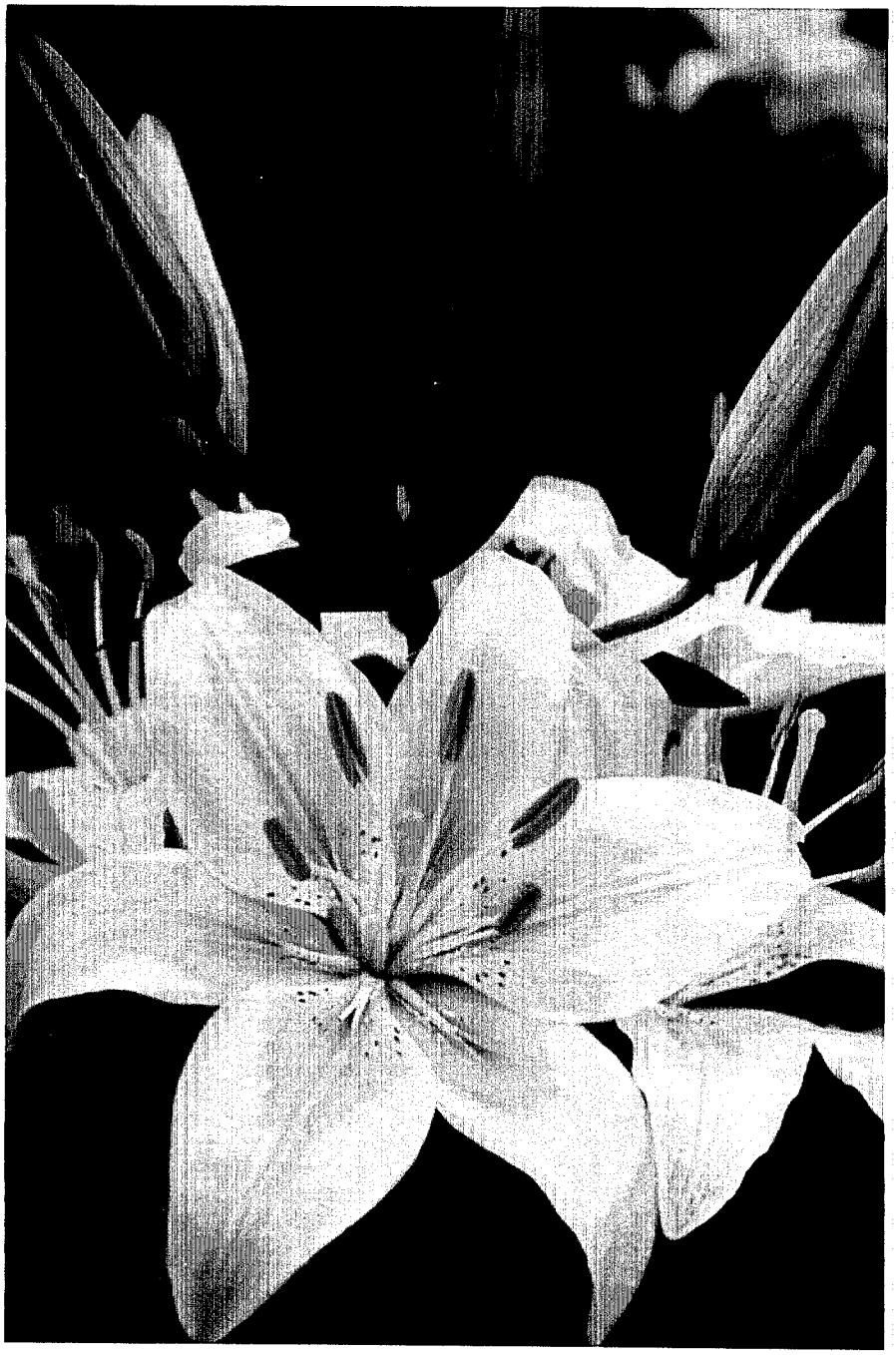

* * * * *